(12) United States Patent
Locke et al.

(10) Patent No.: US 11,766,363 B2
(45) Date of Patent: Sep. 26, 2023

(54) WOUND DRAIN WITH FLUID MANAGEMENT

(71) Applicant: KCI Licensing, Inc., San Antonio, TX (US)

(72) Inventors: Christopher Brian Locke, Bournemouth (GB); James Killingworth Seddon, Ferndown (GB); Benjamin Andrew Pratt, Poole (GB)

(73) Assignee: KCI Licensing, Inc., San Antonio, TX (US)

(*) Notice: Subject to any disclaimer, the term of this patent is extended or adjusted under 35 U.S.C. 154(b) by 645 days.

(21) Appl. No.: 16/091,872

(22) PCT Filed: Apr. 7, 2017

(86) PCT No.: PCT/US2017/026587
§ 371 (c)(1),
(2) Date: Oct. 5, 2018

(87) PCT Pub. No.: WO2017/180467
PCT Pub. Date: Oct. 19, 2017

(65) Prior Publication Data
US 2019/0091388 A1    Mar. 28, 2019

Related U.S. Application Data

(60) Provisional application No. 62/321,380, filed on Apr. 12, 2016.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/79* (2021.05);
(Continued)

(58) Field of Classification Search
CPC .......... A61M 2205/3337; A61M 1/009; A61M 1/0039; A61M 1/00–0098;
(Continued)

(56) References Cited

U.S. PATENT DOCUMENTS 1,355,846 A   10/1920   Rannells
2,547,758 A   4/1951    Keeling
(Continued)

FOREIGN PATENT DOCUMENTS

AU      550575 B2      3/1986
AU      745271 B2      3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Adam Marcetich
*Assistant Examiner* — Meagan Ngo

(57) ABSTRACT

A treatment system for applying negative pressure to a tissue site in conjunction with a venting or purging capability. In some embodiments, the treatment system may include a reduced-pressure source, an inline storage pouch, a purge chamber, and a dressing. Reduced-pressure may be supplied to the inline storage pouch and the dressing, while the purge chamber may provide a ventilation opening to the atmosphere.

14 Claims, 13 Drawing Sheets

(52) U.S. Cl.
CPC ............... *A61M 1/82* (2021.05); *A61M 1/85* (2021.05); *A61M 1/88* (2021.05); *A61M 1/915* (2021.05); *A61M 1/94* (2021.05); *A61M 1/962* (2021.05); *A61M 1/964* (2021.05); *A61M 1/98* (2021.05); A61M 2205/3337 (2013.01); A61M 2205/7518 (2013.01); A61M 2209/088 (2013.01)

(58) Field of Classification Search
CPC .... A61M 2205/7518; A61M 2209/088; A61M 1/964; A61M 1/90; A61F 13/00068; A61F 13/0216
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman |
| 5,215,522 A | 6/1993 | Page |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,439,894 B1 * | 5/2013 | Miller ................. A61F 13/0216 604/319 |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Turney |
| 2007/0009584 A1 * | 1/2007 | Taheri .................. A61M 35/30 424/445 |
| 2007/0219471 A1 | 9/2007 | Johnson et al. |
| 2007/0219532 A1 | 9/2007 | Karpowicz et al. |
| 2007/0265586 A1 * | 11/2007 | Joshi .................. A61F 13/0206 604/313 |
| 2008/0119802 A1 * | 5/2008 | Riesinger .......... A61F 13/00068 604/313 |
| 2009/0030383 A1 * | 1/2009 | Larsen ................. A61M 1/743 604/315 |
| 2010/0305524 A1 * | 12/2010 | Vess ..................... A61F 13/023 604/313 |
| 2011/0224633 A1 * | 9/2011 | Robinson ............ A61M 1/0031 604/319 |

(56) References Cited

U.S. PATENT DOCUMENTS

| | | | |
|---|---|---|---|
| 2012/0316538 A1* | 12/2012 | Heiser | A61M 1/60 604/543 |
| 2014/0039423 A1* | 2/2014 | Riesinger | A61F 13/0203 604/315 |
| 2014/0163491 A1 | 6/2014 | Schuessler et al. | |
| 2014/0330224 A1 | 11/2014 | Albert et al. | |
| 2015/0080788 A1 | 3/2015 | Blott et al. | |
| 2015/0246164 A1* | 9/2015 | Heaton | A61M 1/0031 604/313 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds": Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgl, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinicai Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers ofthe Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, " Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R, 1988) ("Solovev Abstract").

V.A.C.® Therapy Clinicai Guidelines: A Reference Source for Clinicians; Jul. 2007.

PCT/US2017/026587—Written Opinion and Search Report dated Aug. 22, 2017.

\* cited by examiner

WOUND DRAIN WITH FLUID MANAGEMENT

CROSS-REFERENCE TO RELATED APPLICATIONS

This application claims the priority benefit of PCT Application No. PCT/US2017/026587, entitled "WOUND DRAIN WITH FLUID MANAGMENT," filed Apr. 7, 2017, which claims the benefit, under 35 USC 119(e), of the filing of U.S. Provisional Patent Application Ser. No. 62/321,380, entitled "WOUND DRAIN WITH FLUID MANAGEMENT," filed Apr. 12, 2016, all of which are incorporated herein by reference for all purposes.

TECHNICAL FIELD

The invention set forth in the appended claims relates generally to systems for treating tissue sites and processing fluids. More particularly, but without limitation, the present disclosure relates to inline storage pouches, systems, and methods for receiving and storing exudates from a tissue site.

BACKGROUND

Wounds often produce considerable liquids, e.g., exudate. If not properly addressed, liquids at the wound can lead to infection or maceration at or near the wound. Medical wound drainage devices and dressings are often used in wound care to address the production of liquids from the wound. However, common wound drainage devices, system, and methods often face challenges with the drainage of fluids from tissue sites, including the potential for various conduits or other components to become obstructed. Wound drainage devices and dressings may be used alone or as an aspect of applying negative pressure to a tissue site, which may introduce further challenges related to maintaining appropriate target pressure levels and fluid flow, as well as preventing blockages.

Thus, improvements to wound drainage devices, systems, and methods that provide increased fluid management capabilities as well as consistent negative pressure delivery, while reducing the potential for damage to tissue and pain for the patient, are desirable. Such improvements may offer a range of benefits, including reducing the chance of infection, reducing the pooling of fluids, reducing the potential for seroma or hematoma, as well as improving cosmetic appearance.

BRIEF SUMMARY

New and useful systems, apparatuses, and methods for providing wound drainage devices as well as for delivering negative-pressure therapy are set forth in the appended claims. Illustrative embodiments are also provided to enable a person skilled in the art to make and use the claimed subject matter.

In some embodiments, a system for treating a tissue site may include a wound dressing, an inline storage pouch, a reduced-pressure source, and a purge chamber. The inline storage pouch may include a flexible pouch body and a fluid storage material disposed within the flexible pouch body. The purge chamber may be adapted to be fluidly connected to the tissue site and to provide ventilation to the tissue site.

In other example embodiments, a system for treating a tissue site may include a wound dressing, an inline storage pouch, and a reduced-pressure source. The inline storage pouch may include a flexible pouch body having an interior portion, a fluid storage material disposed within the interior portion, a first port formed on the flexible pouch body configured to fluidly connect to a first conduit, a second port formed on the flexible pouch body configured to fluidly connect to a second conduit, and a purge chamber fluidly isolated from the interior portion of the flexible pouch body and adapted to be fluidly connected to a third conduit.

In yet other example embodiments, an inline storage pouch for use with body fluids may include a flexible pouch body having an interior portion, a fluid storage material disposed within the interior portion, a first port formed on the flexible pouch body, a second port formed on the flexible pouch body, and a purge chamber. The purge chamber may be fluidly isolated from the interior portion of the flexible pouch body and may be adapted to be fluidly connected to a third conduit.

In still other example embodiments, a method of storing liquids from a tissue site may include providing an inline storage pouch, coupling the inline storage pouch to the tissue site, coupling the inline storage pouch to a reduced-pressure source, applying negative pressure to the inline storage pouch and the tissue site, and delivering positive pressure from the purge chamber to the tissue site. The inline storage pouch may include a flexible pouch body having an interior portion, a fluid storage material disposed within the interior portion, a first port formed on the flexible pouch body, a second port formed on the flexible pouch body, and a purge chamber fluidly isolated from the interior portion of the flexible pouch body.

In other example embodiments, a system for treating a tissue site may include a wound dressing, an inline storage pouch, a ventilation source, and a reduced-pressure source. The ventilation source may include a purge chamber comprising a vent opening and a purge conduit having a first end connected to the purge chamber and a second end adapted to be placed in fluid contact with the tissue site.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
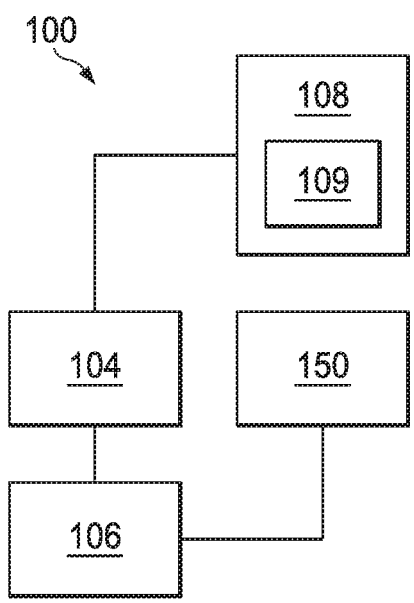
FIG. 1 is a schematic block diagram of an example embodiment of a negative-pressure therapy system for treating a tissue site in accordance with this specification.

FIG. 1 is a schematic, block diagram, showing details of an illustrative embodiment of a therapy system 100 for treating a tissue site with negative pressure. The therapy system 100 may be applied to a human patient as well as used on other types of subjects. The therapy system 100 may include an inline storage pouch, such as pouch 104, a drain apparatus, such as drain 106, and a therapy unit, such as therapy unit 108. Additionally, the therapy system 100 may include a ventilation chamber 150, which may be fluidly coupled to the drain 106.

The pouch 104 may be configured to be mounted to a patient. Similarly, therapy unit 108 may also be configured or tailored to be mounted to a patient. For example, the pouch 104 and/or the therapy unit 108 may be mounted to the patient using one or more straps. The straps may be elastomeric members, belt-like members, or the like. Additionally, the straps may be adjustable, permanently secured, or releasably coupled to pouch 104 and therapy unit 108, respectively. In some embodiments, the straps may allow positioning of pouch 104 and therapy unit 108 at different locations on the patient so that the weight of therapy system 100 may be distributed at more than one location of the patient. For example, pouch 104 may be strapped to a portion of the patient, such as a leg, using straps or other attachment devices. Similarly, therapy unit 108 may be mounted to another portion of the patient, such as around the waist, using additional straps or other attachment means. Pouch 104 and therapy unit 108 may also be mounted at locations other than on a patient, for example, on a bed, pole, or other object.

The pouch 104 is representative of a container, canister, pouch, or other storage component, which can be used to manage exudates and other fluids withdrawn from a tissue site. The pouch 104 may be flexible, allowing the pouch 104 to conform to a portion of the body of patient 102, thereby enhancing the safety and comfort of the patient 102. In addition, the flexible nature of the pouch 104 may allow the pouch 104 to be stored in a small space. The pouch 104 may be relatively easy to manufacture compared to rigid canisters that have been used to collect liquids. Moreover, if the pouch 104 is used with animals, the flexible nature may help prevent injury, for example, if the animal bumps surfaces or rolls over. In addition, the pouch 104 may be oriented as shown in FIG. 1, or the pouch 104 may be oriented in other positions so as to improve fit to, and comfort of, the patient 102. In other embodiments, for example for use of the therapy system 100 in other environments, a rigid container may be preferred for collecting, storing, and disposing of fluids.

The therapy unit 108 may include a negative-pressure source 109, which may be housed within or used in conjunction with the therapy unit 108. In some embodiments, the negative-pressure source 109 may be an electrically-driven vacuum pump. In other illustrative embodiments, the negative-pressure source 109 may be a manually-actuated or manually-charged pump that does not require electrical power. The negative-pressure source 109 may be other types of negative pressure pumps, or may be a wall suction port such as those available in hospitals and other medical facilities.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the drain 106 to the pouch 104 in some embodiments.

In general, components of the therapy system 100 may be coupled directly or indirectly. For example, the negative-pressure source 109 may be directly coupled to the pouch 104, and may be indirectly coupled to the drain 106 through the pouch 104.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a therapeutic environment provided by the drain 106. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 109, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. In some preferred embodiments, the negative-pressure source may be a manually-driven negative-pressure source, such as the Nanova® pump available from Kinetic Concepts, Inc. of San Antonio, Tex. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 109 may be combined with other components into a therapy unit. A negative-pressure supply may also have one or more supply ports configured to facilitate coupling and de-coupling the negative-pressure supply to one or more distribution components.

The ability of negative-pressure systems, such as therapy system 100, to work efficiently can be dependent on the flow of fluids through the various conduits and components included in the system. For example, there are several challenges with drainage of fluids from tissue sites, including the potential for the negative-pressure sources, such as therapy unit 108, and the collection vessels, such as pouch 104, to become clogged. Additionally, in some cases the various conduits connecting the components of negative-pressure systems, such as the first conduit 114 and the second conduit 116, shown at least in FIG. 2a, may be basic tubes and therefore may readily become blocked.

Additionally, in some negative-pressure systems, the negative-pressure source may be in the form of a traditional pressure bulb, as may be apparent to one skilled in the art. When using such traditional pressure bulbs, often times insufficient pressure can be delivered to achieve actual fluid drainage, in addition to the pressure varying as the pressure bulb may fill and re-inflate. As a result, fluid may build up in the surgical space and lead to swelling or infections at the tissue site. Furthermore, traditional pressure bulbs tend to be necessarily small, as they are typically worn close to the tube exit site for sometimes days at a time. As such, the pressure bulbs may have limited fluid capacity, which often requires some patients to wear several bulbs as part of their negative-pressure therapy system. Although the pressure bulbs can be emptied, they may stop draining when they are as little as about 30% full, as at this capacity, there may be virtually no negative pressure being generated. Additionally, because the bulbs may also be used to store the collected wound fluid, as a result of this functionality, the bulbs may need to be emptied when they are primed, or at a minimum, should contain a valve to prevent wound fluid from being pushed back into the wound. Upon entering the pressure bulbs, there is also an increased risk of spillages and contamination, since the wound fluid, including exudates and/or ascites, may be stored in liquid form.

Figure 2A:
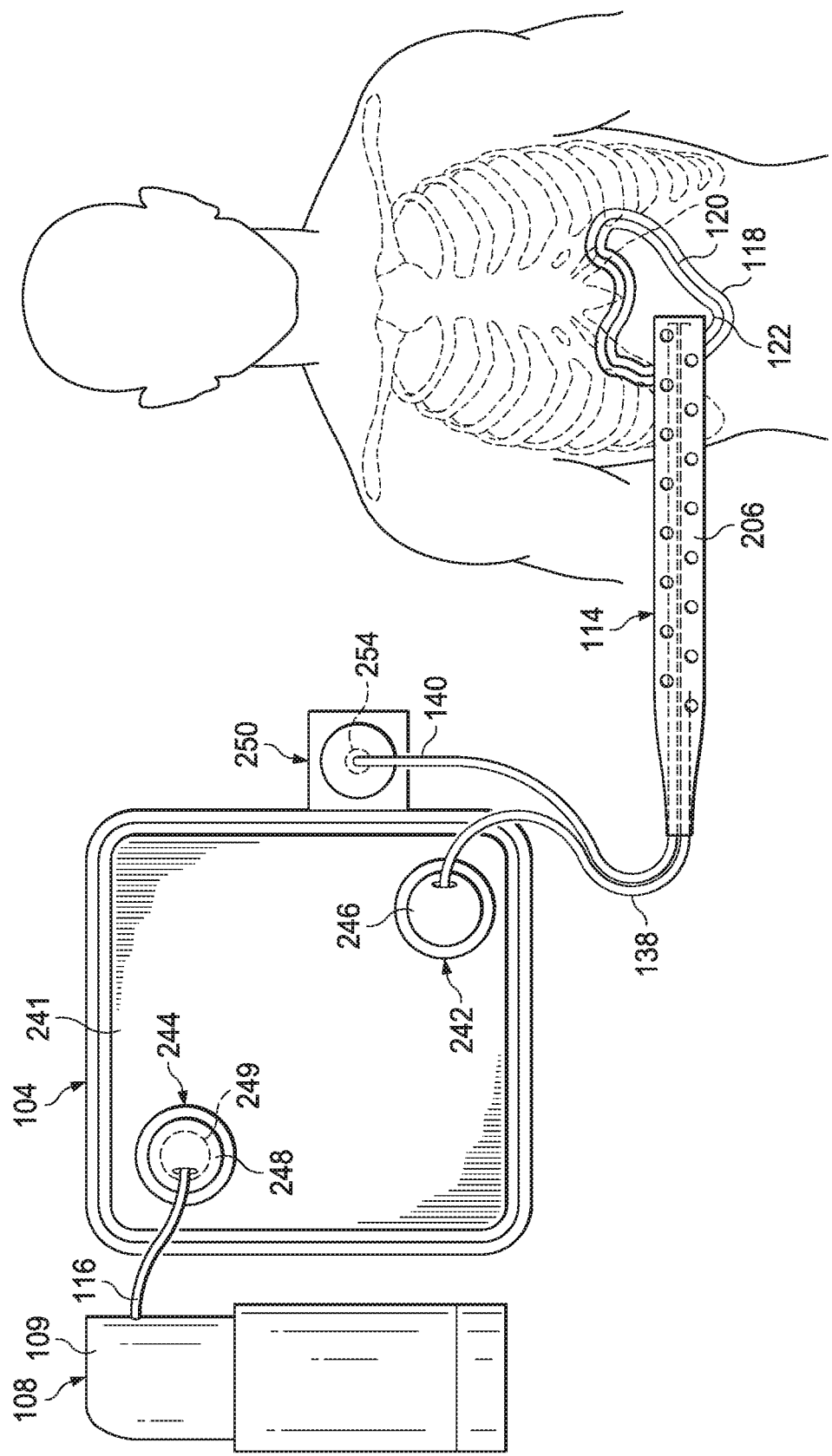
FIG. 2a is a perspective view illustrating additional details that may be associated with some example embodiments of the therapy system of FIG. 1.

As disclosed herein, therapy system 100 can overcome these shortcomings and others by providing a regulated, disposable product solution that may ensure that fluid is removed, while also maintaining an open fluid conduit from the tissue site to the fluid collection device. FIG. 2a is a schematic diagram, illustrating additional details that may be associated with some embodiments of therapy system 100. The drain assembly 206 may be positioned at a tissue site, such as tissue site 118, which extends through the epidermis 120 and the dermis 122.

The term "tissue site" in this context broadly refers to a wound or defect located on or within tissue of a human, animal, or other organism, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, grafts, and fistulas, for example. The term "tissue site" may also refer to areas of tissue that are not necessarily wounded or defective, but are instead areas in which it may be desired to add or promote the growth of additional tissue. For example, negative pressure may be used in certain tissue areas to grow additional tissue that may be harvested and transplanted to another tissue location. The term "tissue site" may also include incisions, such as a surgical incision. Tissue site 118 may include epidermis 120, dermis 122, subcutaneous tissue, or other muscle tissue. Tissue site 118 may be surrounded by healthy or undamaged tissue, for example a portion of epidermis 120 that may be undamaged.

As used herein, the term "coupled" may include direct coupling or indirect coupling via a separate object. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling may include coupling that may permit fluid to be in communication between designated parts or locations. Pneumatic coupling may mean, in part, that gas or gas pressure may be in communication between the designated parts or locations.

In some embodiments, the drain apparatus, such as the drain assembly 206, may be fluidly coupled to the pouch 104 with a first conduit 114, and the pouch 104 may be fluidly coupled to the therapy unit 108 with a second conduit 116. Therapy unit 108 may provide negative pressure, as described in more detail below, through the second conduit 116, the pouch 104, and the first conduit 114 to the drain assembly 206 to remove fluids from a tissue site. Fluids may be delivered to the pouch 104 for storage and later removal. In other embodiments, the fluids may be from an ostomy bag, wound dressing, or another source, rather than the drain assembly 206.

The first conduit 114 may include more than one lumen, such as primary lumen 138 and secondary lumen 140. The first conduit 114 may include the drain assembly 206 at its terminus, which may be configured for placement in fluid, as well as possibly physical, contact with the tissue site 118. As primary lumen 138 may provide negative pressure to the tissue site 118, exudates and other fluids may be drawn through the drain assembly 206 and into the primary lumen 138 of the first conduit 114. Hence, secondary lumen 140 may be configured to be fluidly isolated from primary lumen 138.

In some embodiments, the pouch 104 may be made from two layers of high-moisture-vapor-transmission-rate (high MVTR) polyurethane film welded such that the periphery of the pouch 104 forms a seal to the atmosphere and contains within the pouch 104 a space for collected fluids. For example, the interior of the pouch 104 may include an absorbent structure, such as absorbent bag 241, within the space for collected fluids. The size of the pouch 104 and the corresponding absorbent structure, such as the absorbent bag 241, may vary depending upon design requirements. In some preferred embodiments, the absorbent bag 241 and the pouch 104 may be able to absorb between 40 mL and 150 mL of fluid while maintaining a minimal pressure drop in the therapy system 100.

In some embodiments, the absorbent bag 241 may include or be in the form of a fluid management assembly. The fluid management assembly may include multiple wicking layers as well as an absorbent layer. The absorbent layer may be positioned in fluid communication between a first wicking layer and a second wicking layer. For example, in some exemplary embodiments, a peripheral portion of the first wicking layer may be coupled to a peripheral portion of the second wicking layer to define a wicking layer enclosure between the two wicking layers, in which the absorbent layer may be encapsulated. In some embodiments, the wicking layers may have grains structures adapted to wick fluid along a surface of the wicking layers. For example, the wicking layers may wick or otherwise transport fluid in a lateral direction along the surfaces of the wicking layers. The wicking of fluid along the wicking layers may enhance the distribution of the fluid over a surface area of the absorbent layer, which may increase absorbent efficiency and resist fluid blockages. Fluid blockages may be caused by, for example, fluid pooling in a particular location in the absorbent layer rather than being distributed more uniformly across the absorbent layer. The laminate combination of the wicking layers and absorbent layer may be adapted to maintain an open structure, resistant to blockage, capable of maintaining fluid communication with, for example, the tissue site 118.

The fluid management assembly may include, without limitation, any number of wicking layers and absorbent layers, as desired for treating a particular tissue site. For example, the absorbent layer may be a plurality of absorbent layers positioned in fluid communication between the two wicking layers, as described above. Including additional absorbent layers may increase the absorbent mass of the fluid management assembly and generally provide greater fluid capacity. However, for a given absorbent mass, multiple light coat-weight absorbent layers may be utilized rather than a single heavy coat-weight absorbent layer for providing a greater absorbent surface area for further enhancing the absorbent efficiency. Further, at least one intermediate wicking layer may be disposed in fluid communication between the plurality of absorbent layers. Similar to the absorbent layer described above, the plurality of absorbent layers and the at least one intermediate wicking layer may be positioned within the wicking layer enclosure.

In some embodiments, the absorbent layer(s) may be a hydrophilic material adapted to absorb fluid from, for example, the tissue site 118. Materials suitable for the absorbent layer may include Luquafleece® material, Texsus FP2326, BASF 402C, Technical Absorbents 2317 available from Technical Absorbents (www.techabsorbents.com), sodium polyacrylate super absorbers, cellulosics (carboxy methyl cellulose and salts such as sodium CMC), or alginates. Materials suitable for the wicking layers may include any material having a grain structure capable of wicking fluid as described herein, such as, for example, Libeltex TDL2 80 gsm.

The fluid management assembly may be a pre-laminated structure manufactured at a single location, or alternatively, individual layers of material stacked upon one another as described above. Individual layers of the fluid management assembly may be bonded or otherwise secured to one another without adversely affecting fluid management by, for example, utilizing a solvent or non-solvent adhesive, or by thermal welding.

The pouch 104 may include a first port 242 and a second port 244. In some embodiments, the first port 242 and the second port 244 may be coupled to the same side of pouch 104, while in other embodiments, the first port 242 and the second port 244 may be coupled to different or opposite sides of the pouch 104. In some embodiments, the first port 242 and the second port 244 may be disposed adjacent to opposite ends of the pouch 104, while in other embodiments, the first port 242 and the second port 244 may be disposed adjacent to the same end. In still further embodiments, the first port 242 and the second port 244 may be disposed at other locations of the pouch 104. The first port 242 and the second port 244 may be devices that allow for fluid communication across an outer boundary of the pouch 104 and with an interior of the pouch 104.

In some embodiments, a first pad 246 may be positioned adjacent to the first port 242 on the pouch 104, and may be coupled to or integral with the pouch 104 and/or the first port 242. The first pad 246 may be in fluid communication with the primary lumen 138 of the first conduit 114 and the interior of the pouch 104, and may allow fluid to enter the pouch 104 from the primary lumen 138. A second pad 248 may be positioned adjacent to the second port 244 on the pouch 104, and may be coupled to or integral with the pouch 104 and/or the second port 244. The second pad 248, may be in fluid communication with the interior of the pouch 104 and the second conduit 116. In some embodiments, the second pad 248 may include one or more filters, such as filter 249. The filter 249 may be a hydrophobic filter and/or a charcoal odor filter, which may assist with retaining fluid inside of the pouch 104.

In some embodiments, the first conduit 114 may be fluidly coupled to the first port 242. In the example embodiment illustrated in FIG. 2a, the first port 242 may fluidly couple the primary lumen 138 of the first conduit 114 to the interior of the pouch 104. In some embodiments, the second conduit 116 may be fluidly coupled to the second port 244 and may deliver negative pressure to the pouch 104, which may create a pressure gradient within the interior of the pouch 104. The pressure gradient may move fluids from the first port 242 towards the second port 244, and the fluids may be distributed throughout the interior of the pouch 104 as the negative pressure is applied. Similarly, the primary lumen 138 of the first conduit 114 may deliver negative pressure from the pouch 104 to the drain assembly 206.

In some embodiments, the pouch 104 may optionally also include a conductive feature designed to transmit heat from the patient to the interior of the pouch 104. For example, the patient-facing side of the pouch 104 may be thermally conductive, thus allowing heat from the patient to aid with micro-climate evaporation of fluids captured inside of the pouch 104. In some embodiments, the pouch 104 may include a thermally-conductive layer, at least portions of which may include an adhesive material for placing against a patient. Adjacent to the thermally-conductive layer may be the other component materials of the pouch 104, such as manifold and wicking layers, an absorbent layer, an additional manifold layer, and a high MVTR outer layer. In some embodiments, the high MVTR outer layer may be a 30 micron thick polyurethane film. The thermally-conductive material may be vapor permeable. However, in some embodiments, it may be beneficial for the thermally-conductive material layer to be non-vapor permeable, in order to prevent vapor from migrating to and contacting the patient's tissue, which might otherwise lead to maceration if the pouch 104 is worn on the patient.

Figure 2B:
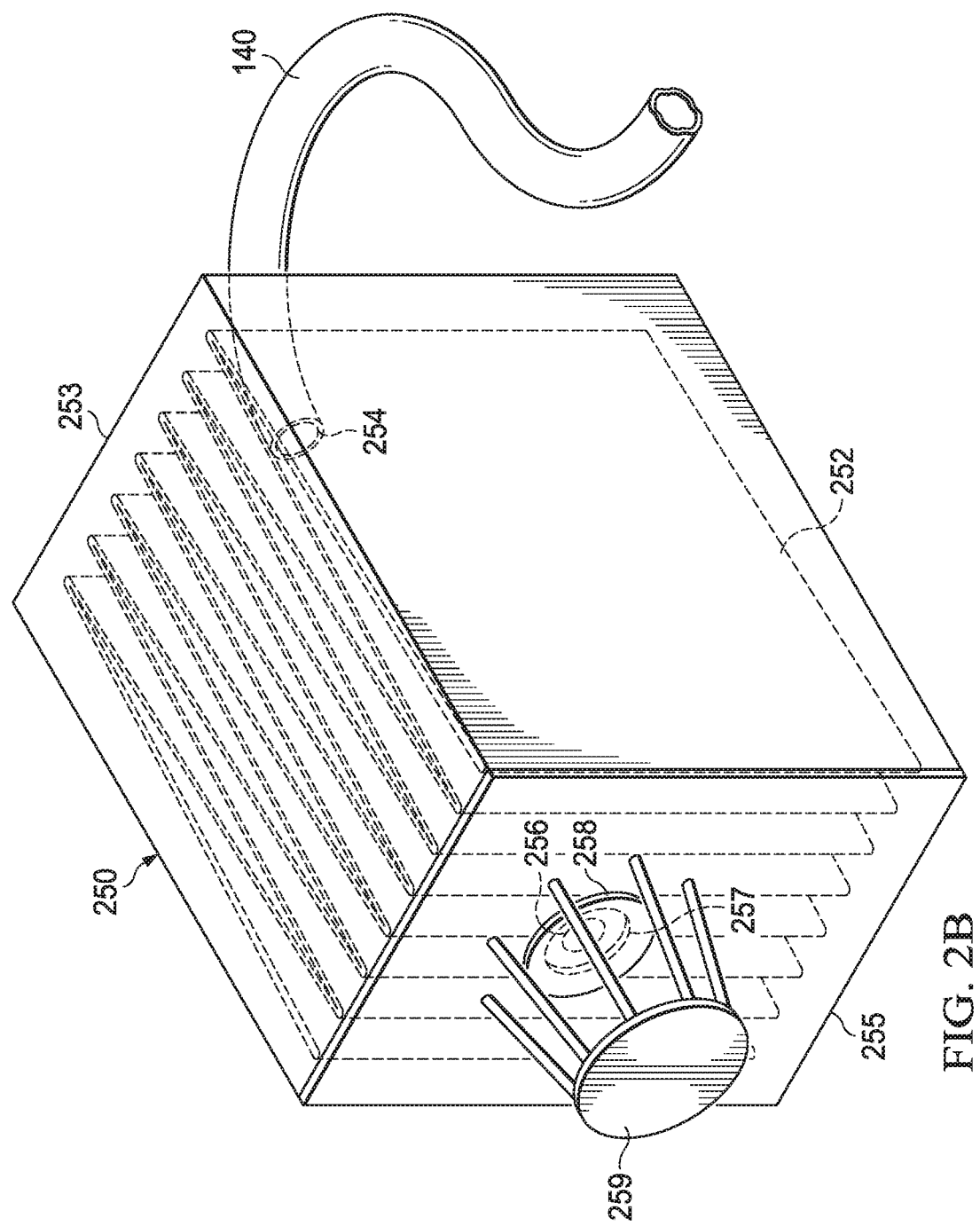
FIG. 2b is an exploded perspective view illustrating additional details that may be associated with some example embodiments of the therapy system of FIGS. 1 and 2.

Referring now also to FIG. 2b, the secondary lumen 140 of the first conduit 114 may be fluidly coupled to a ventilation chamber 250, which may be coupled to the pouch 104, for example through welding. In some embodiments, the ventilation chamber 250 may be enclosed in the material forming the pouch 104, and may be adjacent to the first port 242 on the pouch 104. The ventilation chamber 250 may be fluidly and pneumatically isolated from the fluid collection chamber, such as the absorbent bag 241 of the pouch 104. The ventilation chamber 250 may contain a spacer material 252, which may maintain an open and consistent flow path of fluid inside and through the ventilation chamber 250. In some embodiments, the spacer material 252 may be a foam or non-woven material, such as a polyurethane foam.

The ventilation chamber 250 may include a first wall 253, which may include a first hole 254. In some embodiments, the first hole 254 may be from about 2 mm to 5 mm in diameter. In the embodiment illustrated in FIG. 2b, the hole may be made through the material forming the pouch 104 and the ventilation chamber 250, including the first wall 253. The interior of the ventilation chamber 250 may be fluidly connected to the secondary lumen 140 through the first hole 254, and may further be fluidly connected to the tissue site 118. Some embodiments of the ventilation chamber 250 may include a connector, such as a molded elbow connector, to facilitate the connection of the ventilation chamber 250 to the secondary lumen 140.

The ventilation chamber 250 may include a second wall 255, which may be on the opposite external surface of the ventilation chamber 250 from the first wall 253. The second wall 255 may also include a second hole 256. In some embodiments, the second hole 256 may be from about 0.5 mm to 2 mm in diameter. The second hole 256 may be a single hole, or alternatively, in other embodiments may be a plurality of holes. The outside surface of the material forming the second wall 255 of the ventilation chamber 250 may be covered with a barrier layer 257, which may be formed from the same material as that of the spacer material 252. Additionally, a filter layer 258 may be placed over the barrier layer 257. In some embodiments, the filter layer 258 may be an occlusive, but air-permeable, bacterial membrane material, such as those supplied by GORE, PORVAIR, or GE. The filter layer 258 may be retained in place by an adhesive ring, which may be made from a LOHMANN adhesive. Alternatively, the filter layer 258 may be retained in place using ultrasonic or RF welding. Additionally, in some embodiments, the filter layer 258 may be covered with a protective structure, such as molded protector 259, to prevent occlusion of the filter layer 258 by a user sitting on or otherwise covering the filter layer 258. The filter layer 258, which may be a hydrophobic filter, in combination with the barrier layer 257 and second hole(s) 256, may permit a constant and defined flow of air into the interior of the ventilation chamber 250. For example, in some embodiments, the constant flow of air into the interior of the ventilation chamber 250 may be at a rate in the range of approximately 1-5 cc/hr, and in some embodiments, approximately 5 cc/hr.

Figure 3:
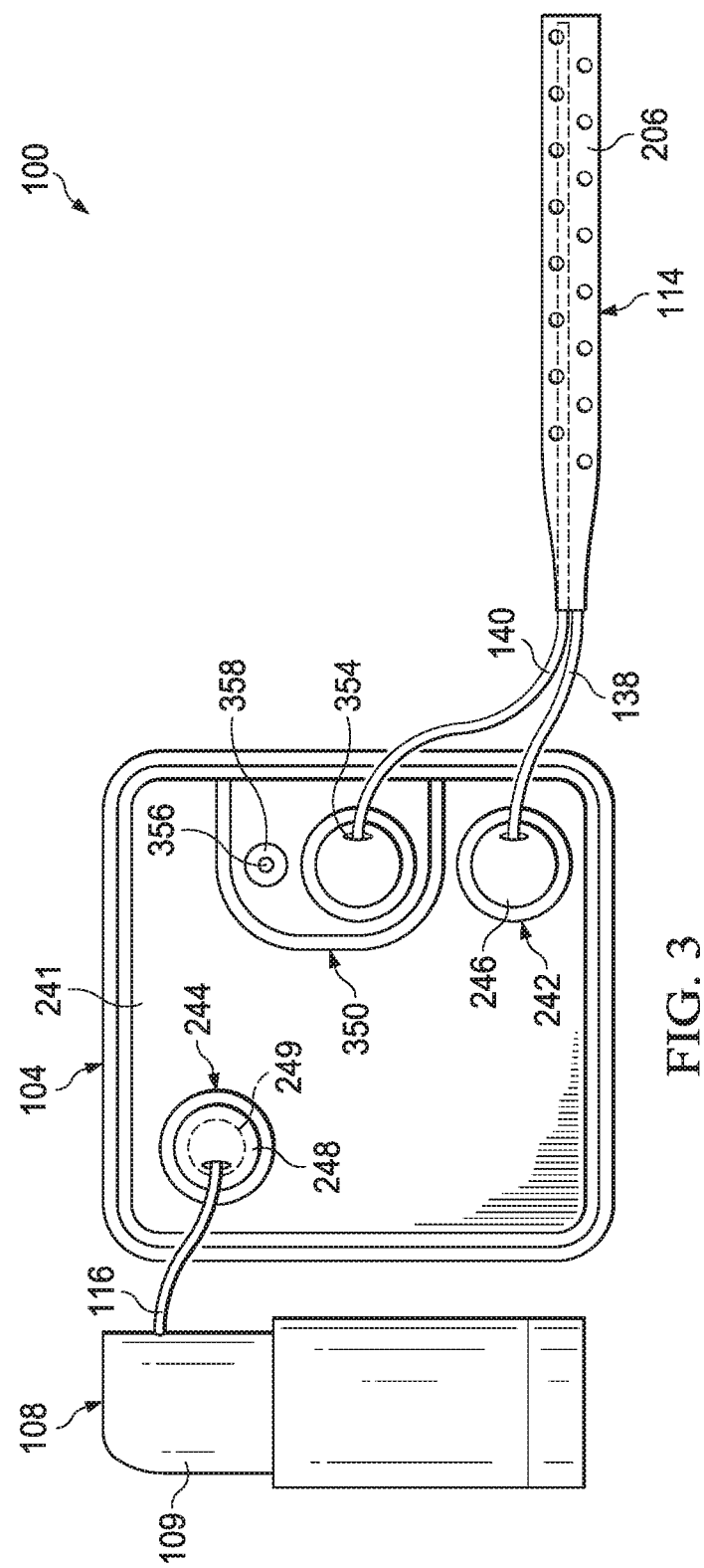
FIG. 3 is a perspective view illustrating additional details that may be associated with some example embodiments of the therapy system of FIG. 1.

FIG. 3 is a schematic diagram, illustrating another example embodiment of therapy system 100. In this example embodiment of therapy system 100, many of the components are the same or analogous as to those of the example embodiment of therapy system 100, as illustrated in FIG. 2a. However, in the example embodiment of therapy system 100 in FIG. 3, the ventilation chamber 350 may be positioned as a separate, isolated portion situated as part of the structure of the pouch 104, rather than being positioned as a separate structure welded or otherwise attached to the pouch 104. The ventilation chamber 350 may include a first hole 354 which may be sized to receive the secondary lumen 140 of the first conduit 114. The ventilation chamber 350 may also include a second hole 356, which in this example embodiment, may be positioned on the same surface as the first hole 354. The second hole 356 may be of substantially the same dimensions and may provide substantially the same purpose and function as the second hole 256, as described above with respect to FIGS. 2a and 2b. Similarly, the second hole 356 may be covered by a microbial filter, such as filter layer 358.

Also similar to the example embodiment of FIGS. 2a, the first conduit 114 may include the primary lumen 138 and the secondary lumen 140. In some embodiments, the first conduit 114 may culminate in a drain assembly, such as drain assembly 206, which may be placed in fluid communication with a tissue site, such as tissue site 118.

Figure 4:
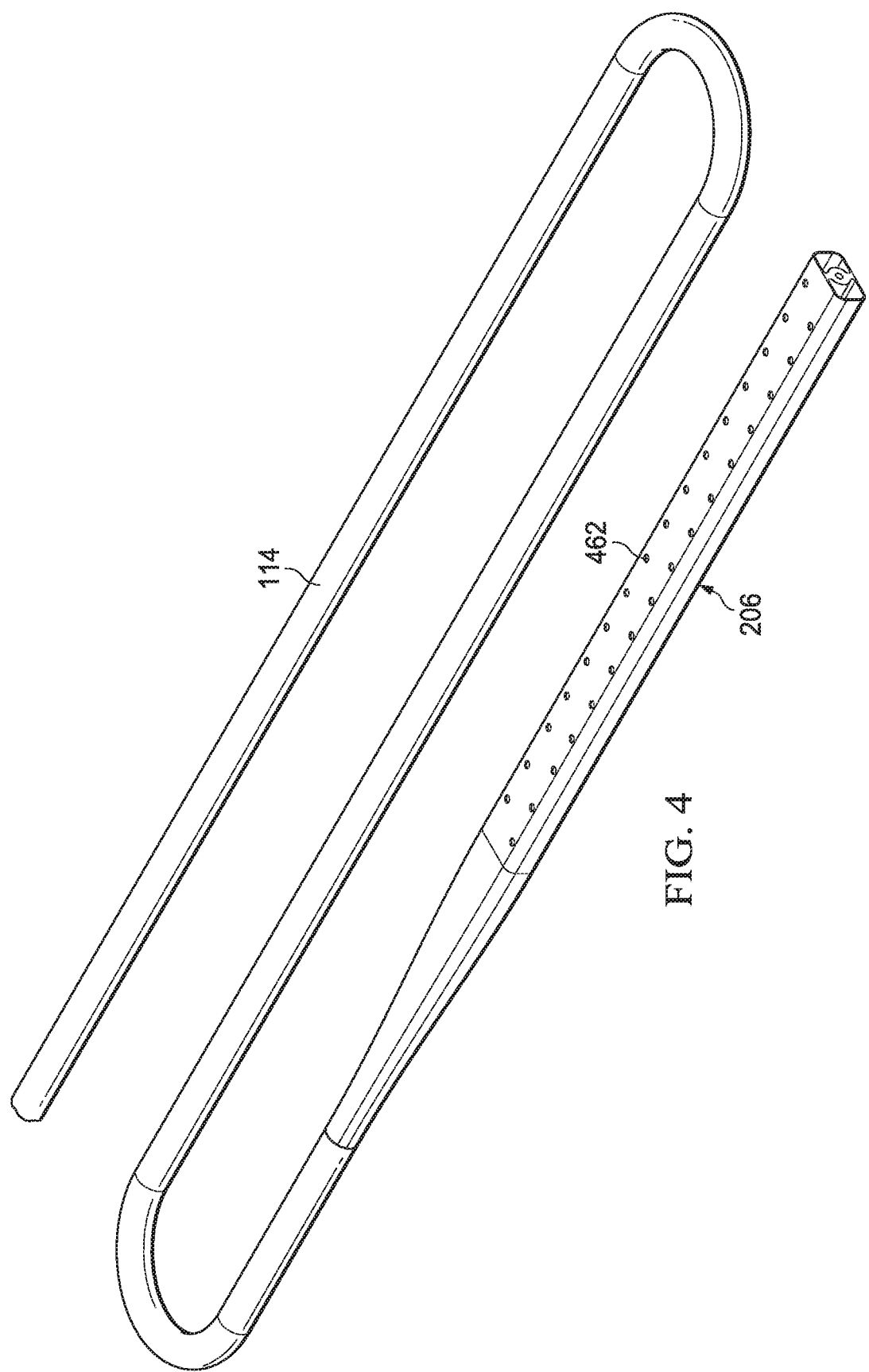
FIG. 4 is a perspective view illustrating additional details that may be associated with some example embodiments of the therapy system of FIG. 3.

As shown in FIG. 4, the drain assembly 206 may include within its structure at least two fluid channels along its length. The drain assembly 206 may also include openings along at least a portion of its length, such as pores 462, for providing fluid communication between a tissue site and the fluid paths of the drain assembly 206.

Figure 5:
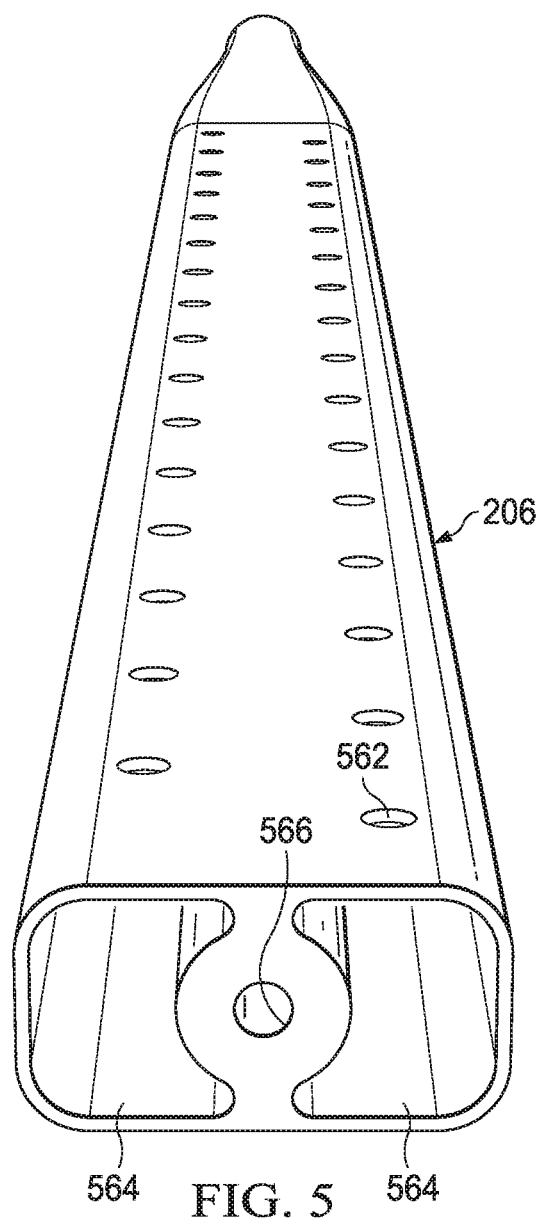
FIG. 5 is a perspective diagram showing a schematic view of additional details that may be associated with features of the therapy system shown in FIG. 4.

Referring now primarily to FIG. 5, the drain assembly 206 may have a central channel extruded through the length of the drain assembly 206, with one or more surrounding channels. The surrounding channels, such as drain conduits 564, may be for the removal of fluids from a tissue site and into a fluid collection chamber, such as the pouch 104. The central channel, such as ventilation conduit 566, may provide a pathway for communication of filtered air from a separate chamber, such as ventilation chambers 250 and 350, as described above, through the secondary lumen 140 of the first conduit 114 and to the end of the drain assembly 206. In some embodiments, the drain assembly 206 may be cut to length as required, while still retaining the arrangement of features hereby discussed.

Figure 6:
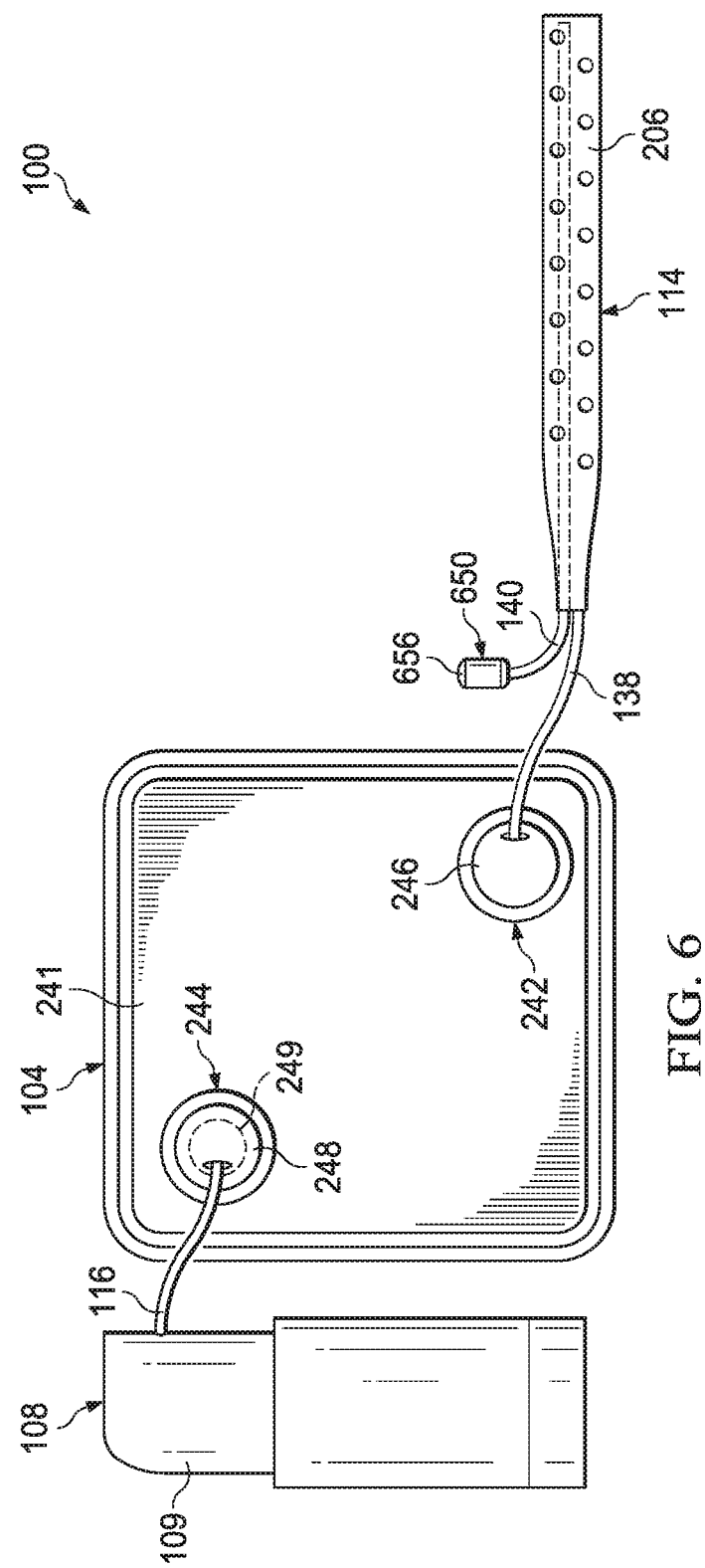
FIG. 6 is a perspective view illustrating additional details that may be associated with some example embodiments of the therapy system of FIG. 1.

In some embodiments, the therapy system 100 may include the programmed leak feature integrated within a drain tube, such as first conduit 114, rather than integrated as a chamber within the fluid collection chamber, such as pouch 104. For example, FIG. 6 illustrates another example embodiment of therapy system 100, in which a ventilation chamber 650 is coupled to the secondary lumen 140. Similar to the embodiments of the ventilation chambers discussed above, ventilation chamber 650 may include a microbial filter 656, which may assist with blocking contaminants from entering the secondary lumen 140 and traveling to the tissue site.

Figure 7:
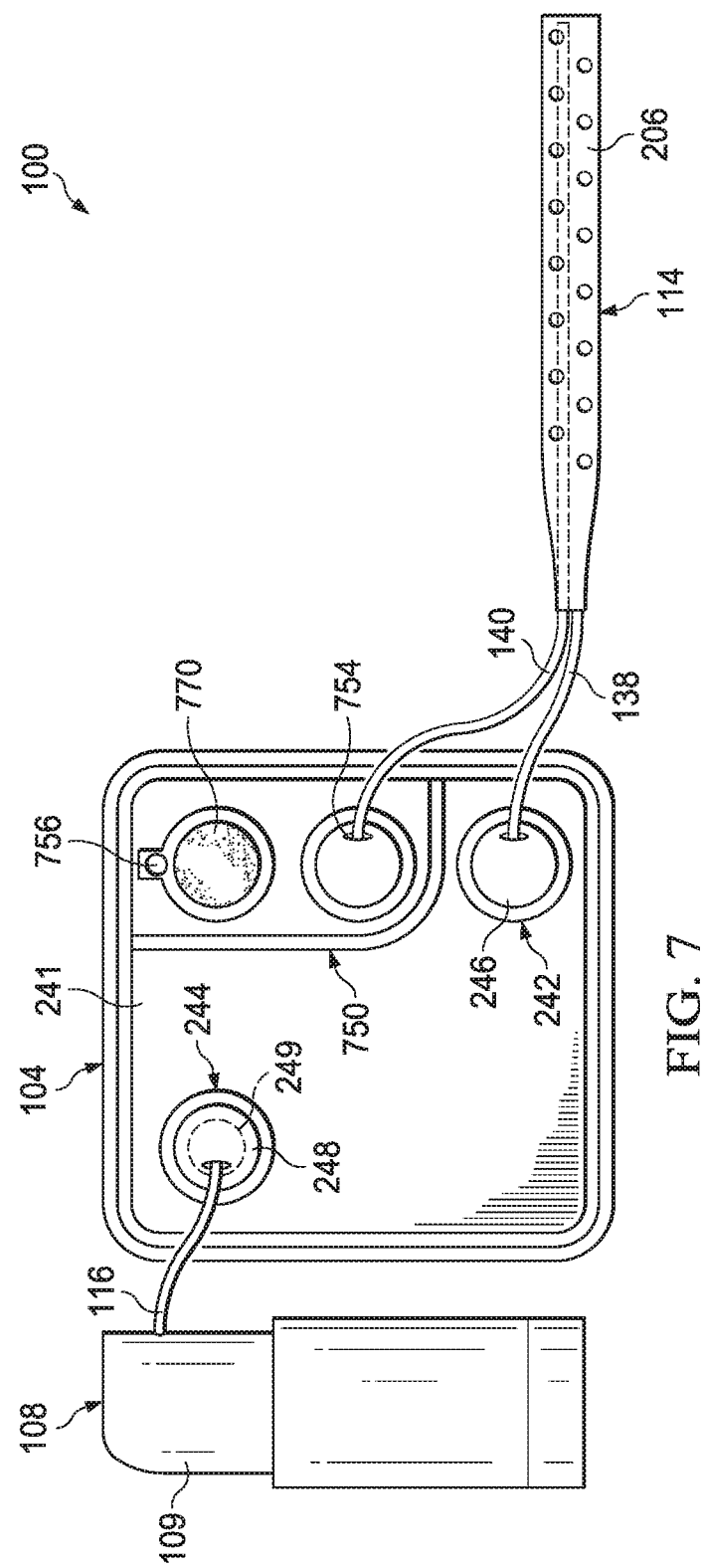
FIG. 7 is a perspective view illustrating additional details that may be associated with some example embodiments of the therapy system of FIG. 1.

FIG. 7 is a schematic diagram, illustrating another example embodiment of therapy system 100, which may include additional features, such as a forced-air purge feature. Similar to the embodiments previously discussed with respect to FIGS. 2a, 2b, and 3, the therapy system 100 may include a purge chamber 750 attached to the pouch 104. In the example embodiment shown in FIG. 7, the purge chamber 750 may be positioned as a separate structure welded or otherwise externally attached to the pouch 104. The purge chamber 750 may include a user-depressible, actuated forced-air purge feature, which can supply additional pressure to a ventilation channel, such as secondary conduit 140, which may pass through the first hole 754. The additional pressure may further be supplied to the drain assembly 206, and the additional pressure may therefore assist with clearing potential blockages and may provide the user with more direct control over the venting feature of the therapy system 100. In this example embodiment, the purge feature may be in the form of purge pump 770, which may be a bulb or other user-depressible structure. A microbial filter, such as those previously discussed with respect to other embodiments, may be integrated within the purge feature. For example, microbial filter 756 may be integrated within purge pump 770, so that air drawn into the purge pump 770 from the atmosphere first passes through the microbial filter 756.

Figure 8:
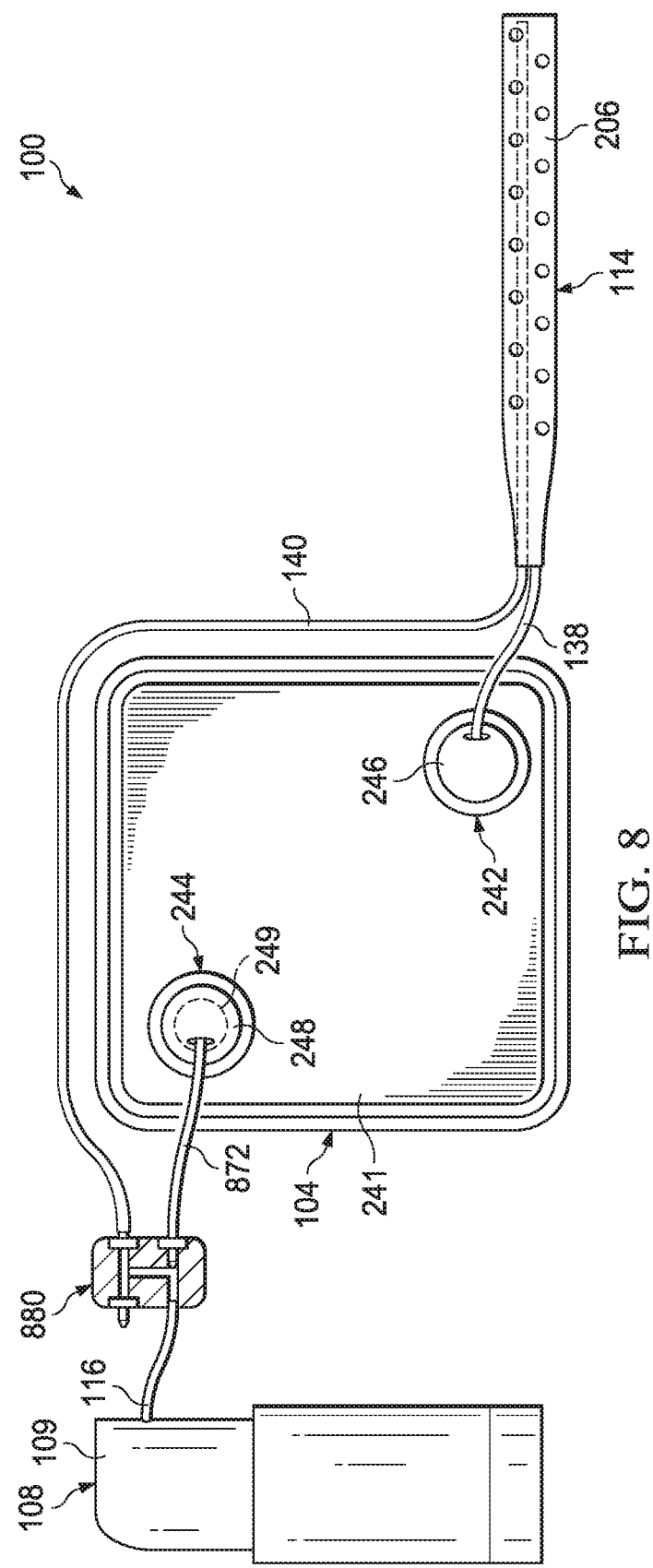
FIG. 8 is a perspective view illustrating additional details that may be associated with some example embodiments of the therapy system of FIG. 1.

FIG. 8 is another schematic diagram, illustrating yet another example embodiment of therapy system 100, which may include an alternative embodiment of the forced-air purge feature. In this example embodiment, the forced-air purge feature may be integrated as part of the conduits of the therapy system 100, and may use the therapy unit 108 as a source of pressure for the purge feature. For example, in some embodiments, the therapy unit 108 may be configured to generate both negative pressure and positive pressure, and the second conduit 116 may be used to alternately deliver both negative pressure and positive pressure from the therapy unit 108 to a chamber with a series of valves, such as purge chamber 880. As depicted in FIG. 8, the purge chamber 880 may be fluidly connected to both the secondary lumen 140 of the first conduit 114 and the second conduit 116. In this arrangement, the purge chamber 880 may be fluidly connected to the negative-pressure source 109 by the second conduit 116 and fluidly connected to the pouch 104 through suction conduit 872. The suction conduit 872 may connect the purge chamber 880 to the second port 244 of the pouch 104.

Figure 9:
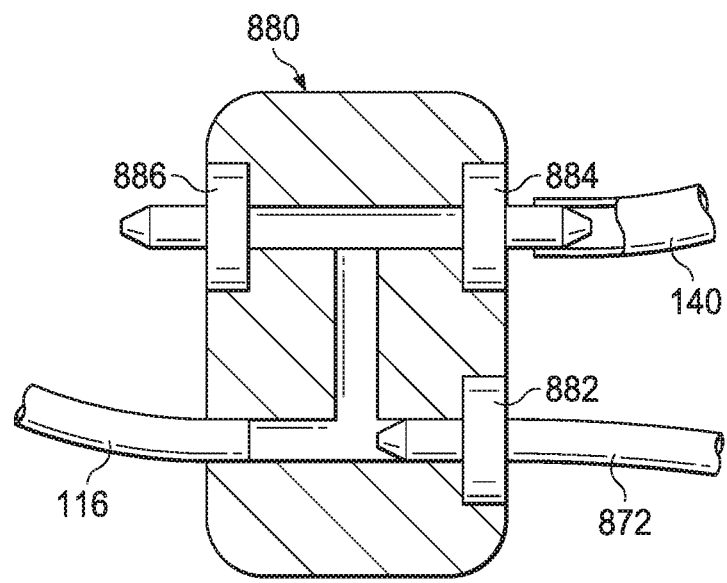
FIG. 9 is a schematic view illustrating additional details that may be associated with features of some example embodiments of the therapy system of FIG. 8.

FIG. 9 is a schematic view of one embodiment of a purge chamber 880. The purge chamber 880 may provide the therapy system 100 with the functionality of being able to cycle between delivering negative-pressure to the pouch 104 and ultimately a tissue site, and a purge phase for relieving the negative pressure and to deliver atmospheric or a greater amount of positive pressure to the secondary lumen 140, drain assembly 206, and ultimately the tissue site. The purge chamber 880 is shown with a series of one-way valves, including a one-way exudate valve 882, a one-way purge valve 884, and a one-way vent valve 886. The one-way exudate valve 882 may be configured so that as a negative-pressure source, such as negative-pressure source 109 of the therapy unit 108, applies a negative pressure to the second conduit 116, the one-way exudate valve 882 is drawn to an open state, thus allowing the negative pressure to be communicated to the suction conduit 872, and ultimately to the pouch 104, the drain assembly 206, and to a tissue site. Simultaneously, as the one-way exudate valve 882 is drawn to an open state, the one-way purge valve 884 and the one-way vent valve 886 may be drawn to a closed position, thus preserving the negative-pressure environment in the purge chamber 880.

In contrast, during the phase of the cycle where negative pressure is not being delivered, or the purge phase of the cycle, the one-way exudate valve 882 may remain in a closed position, thereby minimizing or preventing fluid communication between the therapy unit 108 and the suction conduit 872. During this phase of the cycle, the one-way purge valve 884 may remain at least partially in an open state, and therefore allow the communication of a positive pressure through the second conduit 116 and into the purge chamber 880, and from the purge chamber 880 through the secondary lumen 140 to the drain assembly 206. As positive pressure is applied to the purge chamber 880, through the purge valve 884 and to the secondary lumen 140, the vent valve 886 may function to ensure that the pressure inside the purge chamber 880, the overall therapy system 100, and particularly at the tissue site, does not rise to potentially undesired or harmful levels. For example, in some embodiments, the vent valve 886 may be designed to have a higher threshold pressure required for it to open, as compared to the purge valve 884. Therefore, should the positive pressure in the therapy system 100 reach the threshold pressure of the vent valve 886, the vent valve 886 may partially, or in some cases fully, open to relieve the excess positive pressure in the therapy system 100. The combination of the one-way purge valve 884 and the one-way vent valve 886 may be designed to allow a user, such as a clinician, to positively pressurize, and therefore purge, the fluid lines of the therapy system 100. In order to ensure that the positive pressure does not exceed a pre-defined level, the one-way vent valve 886 may be set to act at a pre-determined safe upper limit of positive pressure. This feature may prevent over-pressurization situations, which may be deemed unsafe. During this phase, the one-way exudate valve 882 will remain in a closed, or at least primarily closed, state, therefore preventing, or at least minimizing, atmospheric or positive pressure from being communicated from the purge chamber 880 into the suction conduit 872 and into the pouch 104.

The series of valves included in the purge chamber may be a variety of different types of valves. For example, in some embodiments, the one-way exudate valve 882 may be a duckbill valve, an umbrella valve, a flap valve, a ball valve, or a disc valve. These types of valves are functionally reliable and designed to be suitable for use with single use products. Similarly, the one-way purge valve 884 and the one-way vent valve 886 may also each be a duckbill valve, an umbrella valve, a flap valve, a ball valve, or a disc valve. However, the one-way purge valve 884 and the one-way vent valve 886 may need to be positioned in an opposite configuration to the one-way exudate valve 882, in order for the purge chamber 880 to provide the intended functionalities. In any of these embodiments, the specific types of valves used in the purge chamber 880 may be adjusted or custom-tailored to provide the desired resistance to pressures as well as flow rates of positive and negative pressures. For example, in some embodiments the cracking pressure on a flap valve may be custom-tailored by adjusting the material and/or geometry of the valve as well as the seat in which the valve is positioned.

Figure 10:
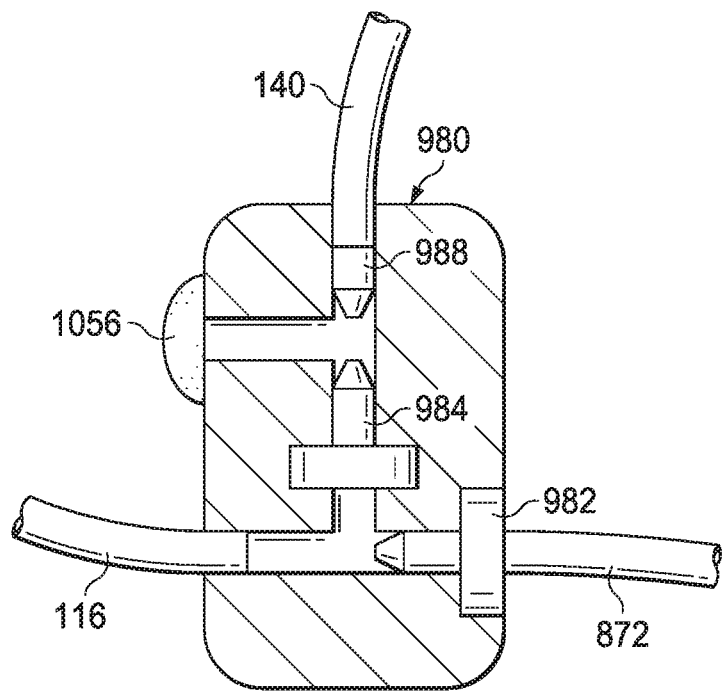
FIG. 10 is a schematic view illustrating additional details that may be associated with features of some example embodiments of the therapy system of FIG. 8.

FIG. 10 is a schematic view of an alternative embodiment of a purge chamber, purge chamber 980. Purge chamber 980 may provide largely the same overall functionality as purge chamber 880 shown in FIG. 9, however may include a different specific arrangement of components, such as valves and filters. For example, in some embodiments, the purge chamber 980 may include a one-way exudate valve 982 and a one-way purge valve 984. In some embodiments, the purge chamber 980 may also include a vent, which may be in the form of a filter, such as microbial filter 1056. In some embodiments, microbial filter 1056 may allow the passage of air from the atmosphere into the purge chamber 980, however may minimize or prevent the passage of harmful particles or pathogens into the purge chamber 980 and other components of the therapy system 100.

In some embodiments, the one-way exudate valve 982 may perform substantially the same function as the one-way exudate valve 882, and may regulate fluid communication between the negative-pressure source 109 and the suction conduit 872. Similarly to the one-way purge valve 884 of the purge chamber 880, the one-way purge valve 984 may oscillate between open and closed positions. For example, during the negative-pressure phase, the one-way purge valve 984 may remain in a closed position, substantially preventing negative pressure from being communicated from the purge chamber 980 into the secondary lumen 140. In contrast, during the vent phase, the one-way purge valve 984 may be drawn to an open position, therefore allowing atmospheric pressure to be communicated from the atmosphere, through the microbial filter 1056, and into the secondary lumen 140, ultimately to the drain assembly 206. In some embodiments, the purge chamber 980 may also include one or more flow restrictors, such as flow restrictor 988. In this example embodiment, flow restrictor 988 may restrict the flow of atmospheric or positive pressure that is communicated from the purge chamber 980 to the secondary lumen 140. In some cases, the flow restrictor 988 may also allow for a better seal when the one-way purge valve 984 is in its closed position. In other embodiments, flow restrictors, such as flow restrictor 988 may be implemented in other portions of the purge chamber 980, such as for example, where the one-way exudate valve 982 is in contact with the suction conduit 872.

For example, when the therapy unit, such as therapy unit 108, is activated, the positive pressure may force the one-way exudate valve 982 into a closed position. The positive pressure may subsequently build up in the purge chamber 980, which may then result in air being forced to pass through the one-way purge valve 984 and into the secondary lumen 140 to provide the purging functionality to the system. In some embodiments, the flow restrictor 988 may act to control the rate of air flow through the secondary lumen 140 and into the wound drain, such as drain assembly 206. For example, if the flow rate of the air is too great, the positive pressure may accumulate in the system, including in the secondary lumen 140 and the purge chamber 980, which may result in the air being vented through the microbial filter 1056. The flow restrictor 988 may also act to control the flow rate of the air leak into the purge chamber 980 and other portions of the system during the negative-pressure phase of the treatment cycle.

Figure 11:
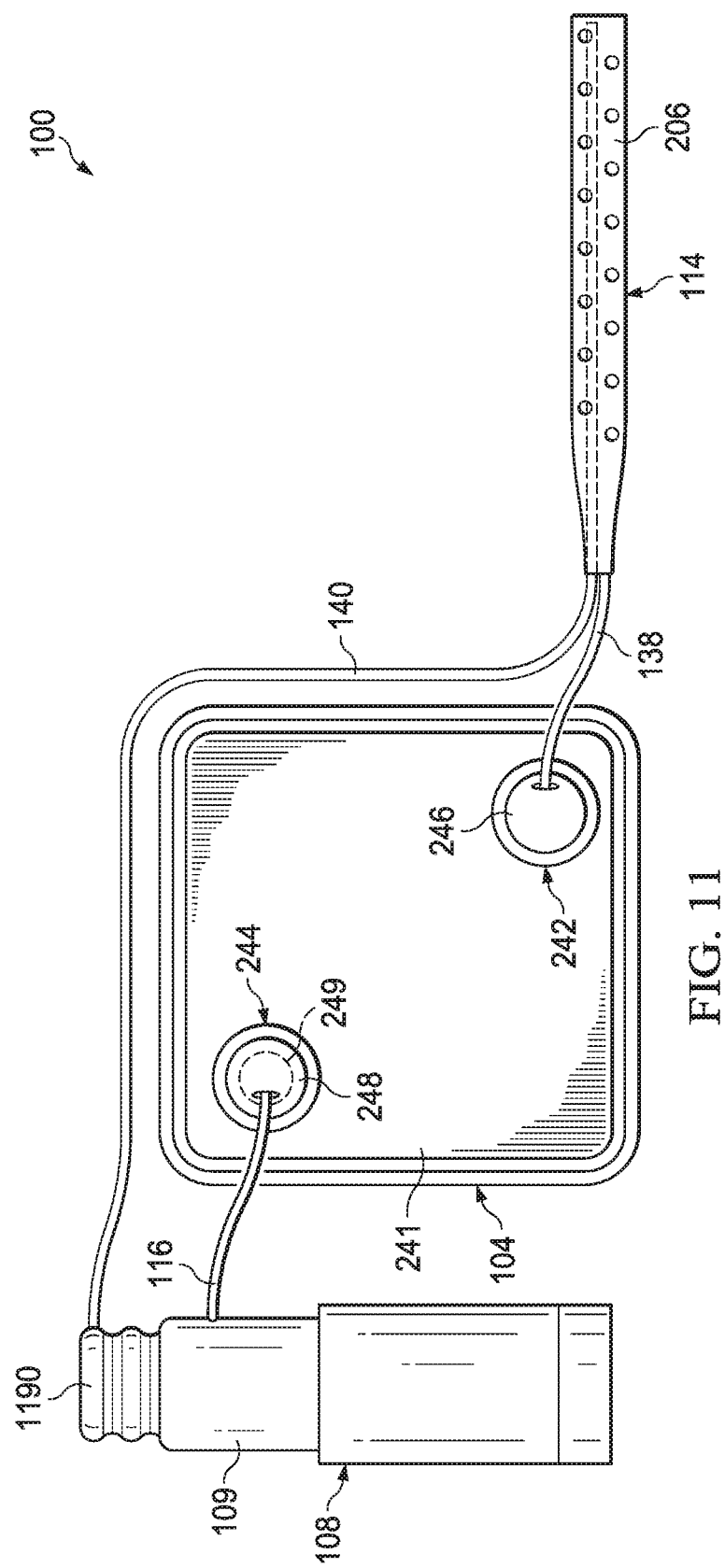
FIG. 11 is a perspective view illustrating additional details that may be associated with some example embodiments of the therapy system of FIG. 1.

FIG. 11 is another schematic diagram, illustrating yet another example embodiment of therapy system 100, which may include another embodiment of the forced-air purge feature. In this example embodiment, the forced-air purge feature may be integrated as part of the therapy unit 108, and may allow a user to directly control the administration of the forced-air to the appropriate components of the therapy system 100. For example, as shown in the embodiment of FIG. 11, the therapy unit 108 may include a user-depressible forced air purge that may be configured to apply increased pressure to an output tube, such as secondary conduit 140, as well as drain assembly 206, in order to clear blockages in the drain assembly 206 and provide a user with an overall increased level of control of the therapy system 100. More specifically, in some embodiments, the therapy unit 108 may include an integrated purge pump, such as integrated purge pump 1190. The integrated purge pump 1190 may be in the form of a variety of different pump configurations, such as a bellows pump, a dome-shaped pump, or a bulb-shaped pump, or any other suitable source of positive pressure. In at least one example embodiment, the integrated purge pump 1190 may be positioned on a top side of the therapy unit 108, so that if a user applies a force to operate the therapy unit 108, the integrated purge pump 1190 may first be compressed. Upon compression of the integrated purge pump 1190, air may be forced through the secondary conduit 140 and into the drain assembly 206, which may assist with clearing any blockages in the drain assembly 206. As the user continues to apply a force to the therapy unit 108, the negative-pressure source 109 of the therapy unit 108 may be activated, which may result in negative pressure being generated and communicated through the second conduit 116 and into the pouch 104.

Figure 12A:
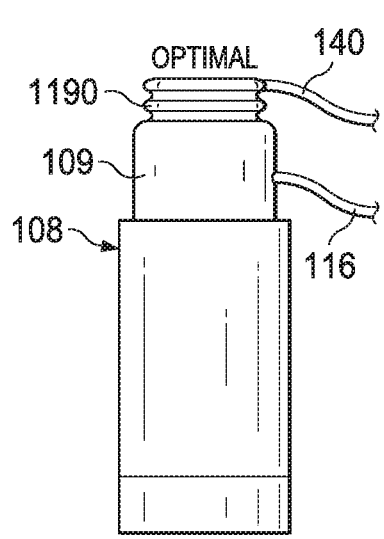
FIGS. 12a-12c are perspective views illustrating additional details that may be associated with some example embodiments of the therapy system of FIG. 11.
Figure 12B:
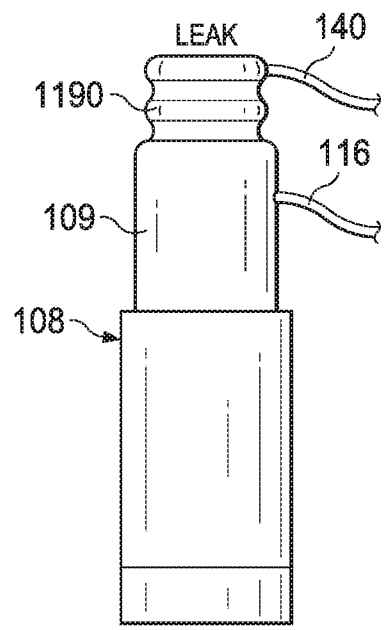
Figure 12C:
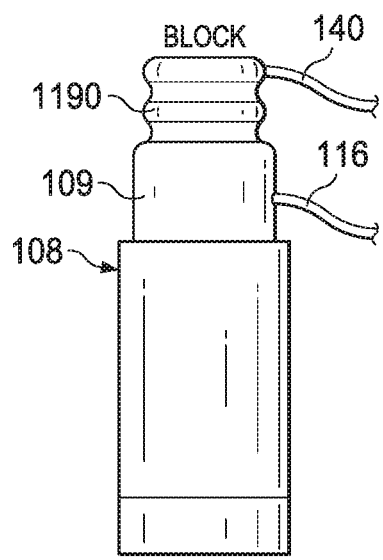

FIGS. 12a-12c are schematic diagrams, illustrating various positions of an integrated purge pump, such as integrated purge pump 1190, as part of the therapy unit 108. The different positions of the integrated purge pump 1190 may provide one or more indications to a user of potential conditions of the therapy system 100. For example, FIG. 12a illustrates a situation where upon pressure applied by a user, the integrated purge pump 1190, as well as the negative-pressure source 109, have been fully depressed. In this situation, it appears as though the system is functioning in an optimal fashion, which may also indicate to a user that there are minimal or no leaks or blockages forming.

In contrast, FIGS. 12b-12c illustrate positions of the integrated purge pump 1190, which may indicate during the negative-pressure therapy phase of the treatment cycle that there is a malfunction in the therapy system 100. For example, FIG. 12b illustrates a situation where a fluid leak may be present in the therapy system 100. In this situation, both the integrated purge pump 1190 and the negative-pressure source 109 remain in uncompressed, or extended, positions, which may indicate that one or more fluid leaks are present in one or more components of the therapy system 100. In another example, FIG. 12c illustrates a situation where a blockage may exist in the therapy system 100. In this situation, while the negative-pressure source 109 remains in a depressed position, the integrated purge pump 1190 remains in an uncompressed position, which may indicate that one or more blockages are present in the fluid communication pathways of the therapy system 100.

Figure 13A:
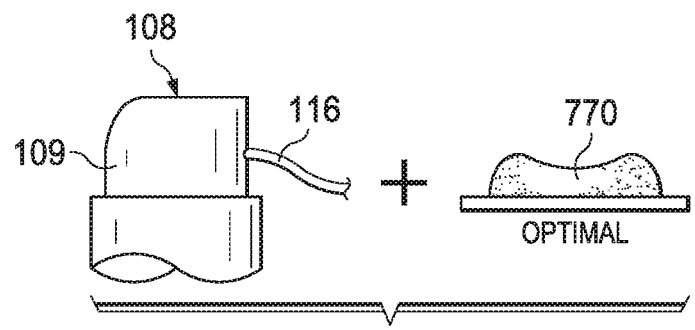
FIGS. 13a-13c are perspective views illustrating additional details that may be associated with some example embodiments of the therapy system of FIG. 11.
Figure 13B:
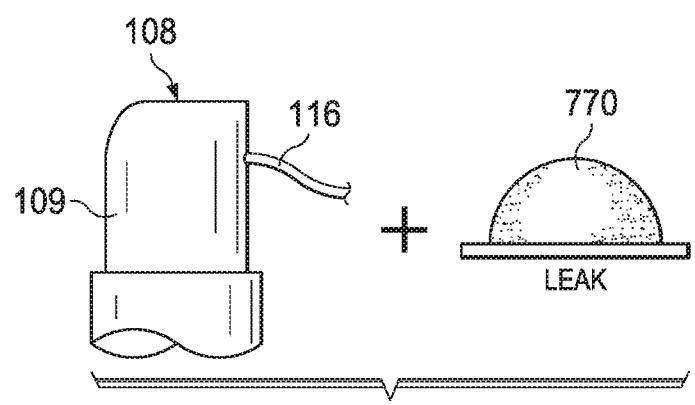
Figure 13C:
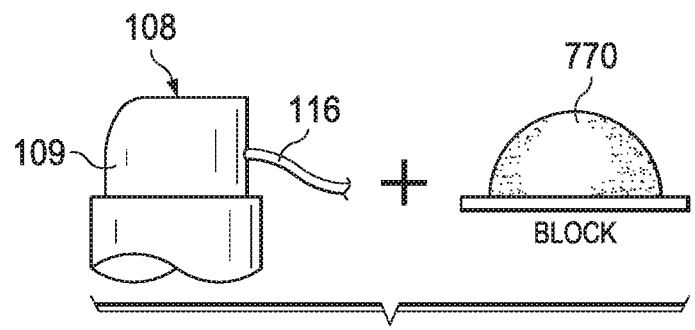

FIGS. 13a-13c are additional schematic diagrams, which also illustrate various positions of the negative-pressure source 109 in conjunction with a purge pump, such as purge pump 770. Similar to the embodiments shown in FIGS. 12a-12c, the different positions of the negative-pressure source 109 and the purge pump 770 may provide one or more indications to a user of potential conditions of the therapy system 100. Analogous to FIG. 12a, FIG. 13a illustrates a situation where upon pressure being applied to the negative-pressure source 109 and the purge pump 770, the negative-pressure source 109 and the purge pump 770 have been fully depressed. Under these conditions, it appears that the therapy system 100 is operating without indications of significant leaks and/or blockages.

Similar to FIGS. 12b-12c, FIGS. 13b-13c provide illustrations of potential situations where one or more fluid leaks and/or blockages may be present in the therapy system 100. FIG. 13b illustrates an example embodiment where the negative-pressure source 109 and the purge pump 770 are in positions which indicate that a fluid leak may exist in the therapy system 100. In this example depiction, both the negative-pressure source 109 and the purge pump 770 remain in uncompressed, or extended, positions. In contrast, FIG. 13c illustrates an example embodiment where the negative-pressure source 109 and the purge pump 770 are in positions which may indicate the presence of a blockage in the fluid pathways of therapy system 100. In this particular depiction, the negative-pressure source 109 remains in a depressed position, while the purge pump 770 remains in an uncompressed, or extended, position.

Figure 14:
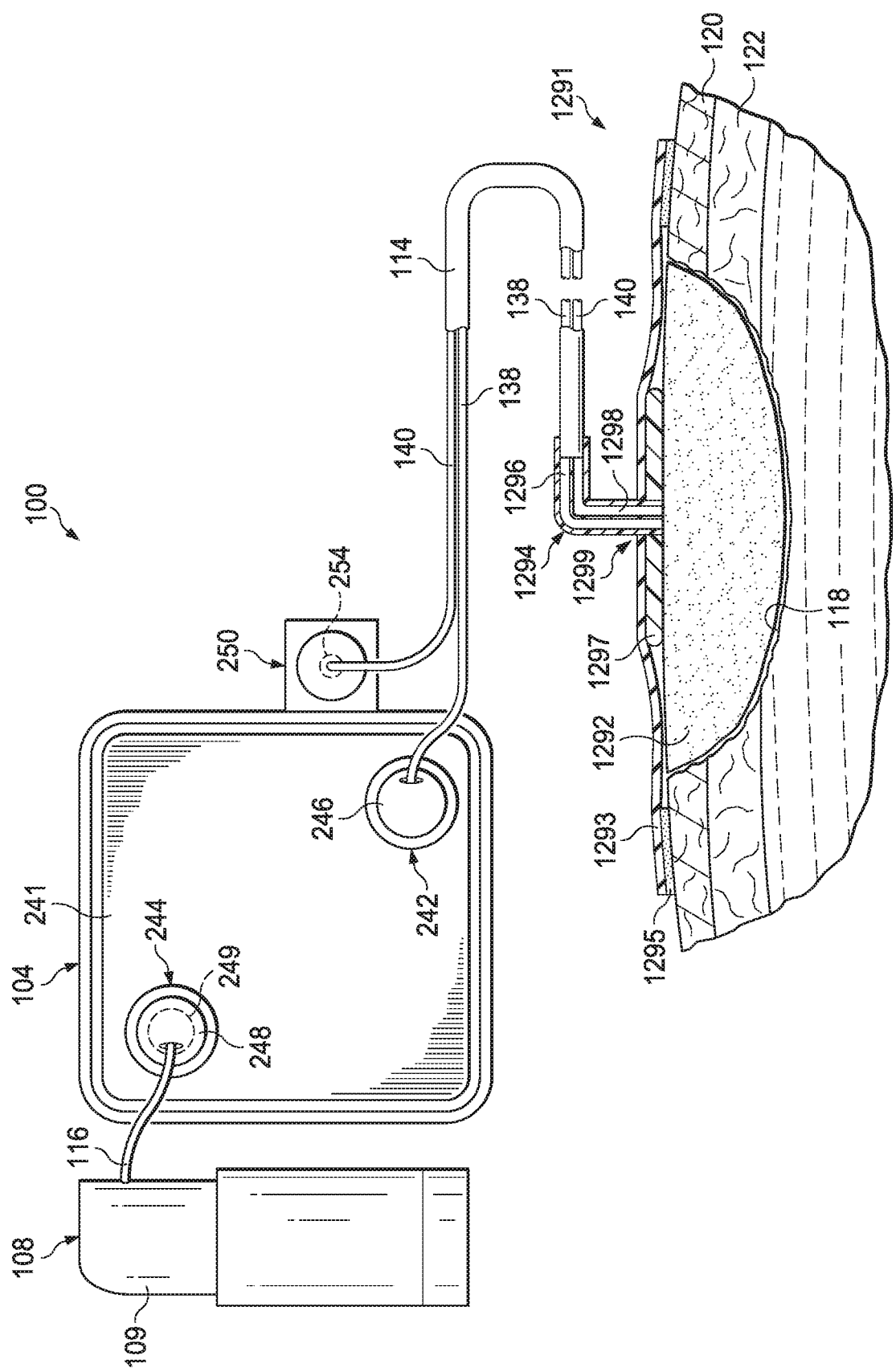
FIG. 14 is a perspective view illustrating additional details that may be associated with some example embodiments of the therapy system of FIG. 1.

FIG. 14 is another schematic diagram, illustrating another example embodiment of therapy system 100. Many of the features and components of this embodiment are similar to or the same as those previously described with respect to FIG. 2a, however rather than including a drain assembly at the terminus of the first conduit 114, the embodiment of the therapy system 100 of FIG. 14 includes a dressing 1291. The dressing 1291 may be positioned at a tissue site, such as tissue site 118, which extends through the epidermis 120 and the dermis 122.

In some embodiments, the dressing 1291 may include a tissue interface, a tissue site covering, and a connector. The tissue interface can be generally adapted to contact a tissue site. The tissue interface may be partially or fully in contact with the tissue site. If the tissue site is a wound, for example, the tissue interface may partially or completely fill the wound, or may be placed over the wound. The tissue interface may take many forms, and may have many sizes, shapes, or thicknesses depending on a variety of factors, such as the type of treatment being implemented or the nature and size of a tissue site. For example, the size and shape of the tissue interface may be adapted to the contours of deep and irregular shaped tissue sites. Moreover, any or all of the surfaces of the tissue interface may have projections or an uneven, course, or jagged profile that can induce strains and stresses on a tissue site, which can promote granulation at the tissue site.

In some embodiments, the tissue interface may be a manifold, such as manifold 1292. The manifold 1292 may be positioned adjacent to, and in contact with, the tissue site 118. The term "manifold" as used herein generally refers to a substance or structure that may be provided to assist in applying negative pressure to, delivering fluids to, or removing fluids from the tissue site 118. Manifold 1292 may include a plurality of flow channels or pathways that can distribute or collect fluids from across the tissue site 118 around manifold 1292. In one illustrative embodiment, the flow channels or pathways may be interconnected to improve distribution of fluids provided to, or removed from, tissue site 118.

The flow channels described herein may be created by voids and/or cells in the manifold 1292 that are fluidly connected to, or in communication with, adjacent voids and/or cells. The flow channels may be uniform in shape and size, or may include patterned or random variations in shape and size. Variations in shape and size of the voids and/or cells of the manifold 1292 may be selectively chosen and used to alter the flow characteristics of fluid and/or exudates through the manifold 1292. For example, in some embodiments, the manifold 1292 may additionally or alternatively comprise projections that form interconnected fluid pathways. In one example, a manifold, such as manifold 1292, may be molded to provide surface projections that define interconnected fluid pathways.

The flow channels described herein allow distribution of negative pressure and/or transportation of exudates and other fluids to and from a particular tissue site. The flow channels provided may be an inherent characteristic of the manifold 1292, provided by a porosity of the manifold 1292, for example, or the flow channels may be chemically, mechanically, or otherwise formed in the material prior to or after assembly of the manifold 1292. The average pore size of the manifold 1292 may vary according to the needs of a prescribed therapy. In some embodiments, the void, pore, or cell sizes of the manifold 1292 described herein may be in the range of about 50 microns to about 600 microns. In other illustrative embodiments, the pore size of the manifold 1292 may be from about 400 microns to about 600 microns. The tensile strength of the manifold 1292 may also vary according to the needs of a prescribed therapy. For example, the tensile strength of a manifold comprising a foam may be increased for delivery of topical treatment solutions.

Manifold 1292 may be a biocompatible material adapted to be placed in contact with tissue site 118 and distribute negative pressure across tissue site 118. Examples of manifold 1292 may include, without limitation, devices that have structural elements arranged to form flow channels, such as, for example, cellular foam, open-cell foam, porous tissue collections, liquids, gels, and foams that include, or cure to include, flow channels. Manifold 1292 may be porous and may be made from foam, gauze, felted mat, or other material suited to a particular biological application. In one embodiment, manifold 1292 may be a porous foam and may include a plurality of interconnected cells or pores that act as flow channels. The porous foam may be a polyurethane, open-cell, reticulated foam such as GranuFoam® material or VeraFlo® foam, both available from Kinetic Concepts, Inc. of San Antonio, Tex. In some embodiments, manifold 1292 may also be used to distribute fluids such as medications, antibacterials, growth factors, and other solutions to tissue site 118. Other layers may be included in or on manifold 1292, such as absorptive materials, wicking materials, hydrophobic materials, and hydrophilic materials.

The manifold 1292 may be either hydrophobic or hydrophilic. In an example in which the manifold 1292 may be hydrophilic, the manifold 1292 may also wick fluid away from a tissue site, while continuing to distribute negative pressure to the tissue site. The wicking properties of the tissue interface, such as the manifold 1292, may draw fluid away from a tissue site by capillary flow or other wicking mechanisms. An example of a hydrophilic foam is a polyvinyl alcohol, open-cell foam such as V.A.C. WhiteFoam° dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 1292 may further promote granulation at a tissue site when pressure within the sealed therapeutic environment is reduced. For example, any or all of the surfaces of the manifold 1292 may have an uneven, coarse, or jagged profile that can induce microstrains and stresses at a tissue site if negative pressure is applied through the manifold 1292.

In one illustrative embodiment, manifold 1292 may be constructed from bioresorbable materials that do not have to be removed from tissue site 118 following use of the therapy system 100. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. Manifold 1292 may further serve as a scaffold for new cell-growth, or a scaffold material may be used in conjunction with manifold 1292 to promote cell-growth. A scaffold may be a substance or structure used to enhance or promote the growth of cells or formation of tissue, such as a three-dimensional porous structure that may provide a template for cell growth. Illustrative examples of scaffold materials include calcium phosphate, collagen, PLA/PGA, coral hydroxy apatites, carbonates, or processed allograft materials. Scaffold materials may have pore sizes that are large enough to permit ingrowth of tissue into the scaffold. In some embodiments, the pore sizes may be in an upper end of the range of pore sizes of the manifold materials described above.

In some embodiments, the tissue site covering may be a drape, such as drape 1293. The drape 1293 may at least partially cover the manifold 1292 if positioned over the tissue site 118, and a drape aperture 1299 may extend through the drape 1293. In some embodiments, the drape 1293 may provide a bacterial barrier and protection from physical trauma. The drape 1293 may provide a fluid seal adequate to maintain negative pressure at a desired site given a particular reduced-pressure source or subsystem involved.

In some embodiments, the drape 1293 may be, for example, an impermeable or semi-permeable, elastomeric material. An elastomeric material generally refers to a polymeric material that may have rubber-like properties. More specifically, most elastomers may have ultimate elongations greater than 100% and a significant amount of resilience. The resilience of a material refers to the material's ability to recover from an elastic deformation. Elastomers that are relatively less resilient may also be used as these elastomers are more likely to tear if faced with a cutting element. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of materials of drape 1293 may include a silicone drape, 3M Tegaderm® drape, and a polyurethane (PU) drape such as one available from Avery Dennison Corporation of Pasadena, Calif. An additional, specific non-limiting example of a material of drape 1293 may include a 30 µm matte polyurethane film such as the Inspire™ 2317 manufactured by Exopack™ Advanced Coatings of Matthews, N.C.

The drape 1293 may have a high moisture-vapor transmission rate (MVTR) in some applications. For example, the MVTR may be at least 300 g/m² per twenty-four hours in some embodiments. In some example embodiments, the drape 1293 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device, such as attachment device 1295 may be used to attach the drape 1293 to an attachment surface, such as undamaged epidermis, a gasket, or another cover. The attachment device 1295 may fluidly seal the drape 1293 to undamaged epidermis so that fluid may be inhibited from passing between the drape 1293 and the epidermis.

The attachment device 1295 may take many forms. For example, the attachment device 1295 may be a medically-acceptable, pressure-sensitive adhesive that extends about a periphery, a portion, or the entire drape 1293. In some embodiments, for example, some or all of the drape 1293 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, organogel, or other sealing devices or elements. In yet other example embodiments, the attachment device 1295 may also be a sealing ring or other device. In still another example, the attachment device 1295 may be a releasable adhesive material capable of being removed from the tissue site and reapplied to tissue site. Before use, a drape adhesive may be covered by a release liner (not shown) to protect the drape adhesive before being applied to tissue site.

In some embodiments, a dressing interface, such as connector 1294, may facilitate coupling the dressing 1291 to the first conduit 114 and the pouch 104. In some embodiments, connector 1294 may be a disc-like member having a first side and a second side. In one illustrative embodiment, connector 1294 may be a T.R.A.C.® Pad or Sensa T.R.A.C.® Pad available from KCI of San Antonio, Tex. Connector 1294 may allow the negative pressure to be delivered to the dressing 1291. In other exemplary embodiments, connector 1294 may also be a conduit inserted through drape 1293.

In some embodiments, the connector 1294, may include a flange 1297, a primary connector lumen 1296, and a secondary connector lumen 1298. Flange 1297 may be a base member or other suitable device configured to couple connector 1294 to another body, such as manifold 1292 or drape 1293. In some embodiments, flange 1297 may couple connector 1294 to manifold 1292 as shown. In other embodiments, flange 1297 may include a flange adhesive applied to a surface of flange 1297 so that flange 1297 may couple connector 1294 to drape 1293. Flange 1297 may be disposed between drape 1293 and manifold 1292 as shown, or in another embodiment, flange 1297 may be disposed on drape 1293 opposite manifold 1292.

As already discussed, the first conduit 114 may include more than one lumen, such as a primary lumen 138, and a secondary lumen 140. The first conduit 114 may be coupled to connector 1294, which may thus enable primary lumen 138 to be in fluid communication with the primary connector lumen 1296 and secondary lumen 140 to be in fluid communication with the secondary connector lumen 1298. As primary lumen 138 may provide negative pressure to the tissue site 118, exudates and other fluids may be drawn through primary connector lumen 1296 and into primary lumen 138. As previously discussed, secondary lumen 140 may be configured to be fluidly isolated from primary lumen 138.

In some embodiments, the primary connector lumen 1296 may receive negative pressure through first conduit 114 and may supply negative pressure to manifold 1292. In some embodiments, the secondary connector lumen 1298 may be for providing ventilation of the tissue site 118 to the atmosphere, or alternatively, for providing a positive pressure to the tissue site 118. In other embodiments, the secondary connector lumen 1298 may be a sensing lumen configured to communicate negative pressure at manifold 1292 to an instrumentation unit, such as therapy unit 108, to determine the pressure at manifold 1292.

In operation, the therapy system 100, such as the embodiment disclosed in FIG. 2a, may be used in accordance with many of the principles already described. For example, the drain assembly 206 may be installed proximate to the tissue site, and the first conduit 114 routed from the drain assembly 206 to the pouch 104, which may be taped or adhered using silicone, polyurethane, or acrylic adhesive to the patient close to the tissue site. For example, in the case of a breast surgery, the pouch 104 may be attached to the lower abdomen. Negative pressure applied across the tissue site 118 can remove exudates and other fluids from the tissue site 118, which can be collected in a container, such as the pouch 104.

The drain assembly 206 may be connected to the pouch 104 through the first conduit 114, and the pouch 104 may be located on a patient using an appropriate fixation device, for example, straps, elastic bands, or adhesive fixations. The pouch 104 may be in turn connected to the therapy unit 108. The negative-pressure source 109 of the therapy unit 108 may then be used to deliver negative pressure to the pouch 104 and the tissue site 118. For example, in some preferred embodiments, the negative-pressure source 109 may be a manually-compressible pump. In some embodiments, the manually-compressible pump may be the Nanova® pump, commercially available from Kinetic Concepts Inc. of San Antonio, Tex. In some embodiments, it may be desirable to modify the Nanova® pump to adjust the magnitude of the pressure output. For example, while the unmodified Nanova® pump typically may deliver a regulated 125 mmHg, it may be advantageous to modify the pump to deliver a lower pressure, if therapeutically beneficial. In such cases, it may be necessary to modify the internal regulator spring and the charge chamber spring of the Nanova® pump in order to lower the overall pressure capacity of the negative-pressure source 109. Further fine tuning may be warranted to best tailor the amount of applied negative pressure and flow rates of fluid in the therapy system 100, based on the particular type of tissue site being treated.

As the negative-pressure source 109 is charged, air may be removed from the pouch 104 and ultimately the tissue site. Upon generating this negative-pressure environment in the pouch 104, a steady-state situation may be achieved where negative-pressure is further communicated to the drain assembly 206. Fluids may then be drawn from the tissue site, such as a wound, through the drain assembly 206 and the first conduit 114, and into the pouch 104 where the fluids may be absorbed and/or immobilized.

During operation, the filter, such as microbial filter 258, in the ventilation chamber 250 of the pouch 104 may permit a small, constant flow of filtered air through the secondary lumen 140 to the distal end of the drain assembly 206 and in contact with the tissue site 118. The air may then be drawn back up the fluid conduits 564, as depicted in FIG. 5, of the drain assembly 206, through the first conduit 114, through the pouch 104 and eventually into the negative-pressure source 109 of the therapy unit 108. As such, the purpose of the constant flow of air may be to prevent the drain from blocking and occluding flow. However, one consequence of this gradual, constant flow of air is that the negative-pressure source 109 may need to be recharged approximately every 8 hours. This recharge may also serve as an indicator to the user, such as the patient or caregiver, that the fluid passageways of the therapy system 100 are not blocked, since if there is no flow of air, the negative-pressure source 109 will likely not need recharging.

The systems, apparatuses, and methods described herein may provide significant advantages, some of which have already been discussed. For example, the therapy systems discussed may store fluid in a wearable, conformable, and breathable inline pouch, which may be adapted to be of various sizes and shapes to aid with application and compliant usage. Additionally, in some embodiments, the inline pouch may be able to make use of the patient's body head to better evaporate fluids from the pouch, thereby increasing the capacity of the pouch. The constant flow of filtered air through the drain assembly may prevent or reduce the occurrence of blockages in the drain assembly as well as conduits of the therapy system, thus better ensuring that fluids are removed from the tissue site. Furthermore, in embodiments of the therapy system incorporating the Nanova® pump, the operation of the Nanova® pump may provide an indication of whether the drain assembly and conduits are blocked as well as if the pouch is full. Additionally, the drain assembly may be sized (shortened) without impeding the performance of the therapy system, including the constant flow of filtered air through the drain assembly.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the drain assembly 106, the pouch 104, or both may be eliminated or separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, comprising:
a wound dressing for disposing proximate to the tissue site;
an inline storage pouch comprising a flexible pouch body and a fluid storage material disposed within the flexible pouch body;
a reduced-pressure source adapted to supply negative pressure to the inline storage pouch and the wound dressing; and
a purge chamber directly coupled to an exterior surface of the flexible pouch body and adapted to be fluidly connected to the tissue site and to provide flow of air from atmosphere to the tissue site for ventilation.

2. The system of claim 1, wherein the purge chamber further comprises a vent opening to the atmosphere.

3. The system of claim 2, wherein the purge chamber further comprises a microbial filter adapted to be positioned over the vent opening.

4. The system of claim 1, wherein the purge chamber is configured to deliver a constant flow of ventilation to the tissue site.

5. The system of claim 1, further comprising a drain assembly adapted to be positioned adjacent the tissue site, wherein the drain assembly comprises a plurality of openings, and wherein the drain assembly is not directly coupled to the purge chamber.

6. The system of claim 1, further comprising a purge conduit adapted to fluidly connect the purge chamber to the tissue site.

7. The system of claim 1, further comprising:
a drain assembly adapted to be positioned adjacent the tissue site, wherein the drain assembly comprises a plurality of openings, and wherein the drain assembly is not directly coupled to the purge chamber; and
a purge conduit adapted to fluidly connect the purge chamber to the tissue site, wherein at least a portion of the purge conduit is disposed within the drain assembly.

8. The system of claim 1, wherein the wound dressing comprises a drape adapted to provide a fluid seal over the tissue site.

9. The system of claim 1, further comprising a purge pump adapted to provide a positive pressure to the tissue site.

10. The system of claim 9, wherein the purge pump is a bellows pump.

11. The system of claim 1, wherein the purge chamber comprises one or more one-way valves.

12. The system of claim 1, wherein the reduced-pressure source comprises a manually-actuated reduced-pressure pump.

13. The system of claim 12, wherein the manually-actuated reduced-pressure pump is adapted to supply a therapy pressure of between about −125 mmHg and −45 mmHg.

14. The system of claim 1, wherein the purge chamber is fluidly isolated from an interior of the flexible pouch body.

* * * * *